United States Patent
Boulanger et al.

(10) Patent No.: US 11,998,531 B1
(45) Date of Patent: Jun. 4, 2024

(54) PHARMACEUTICAL INTERMEDIATES AND METHODS FOR PREPARING THE SAME IN THE SYNTHESIS OF MUSCIMOL AND CONGENERS AND DERIVATIVES THEREOF

(71) Applicants: William Allen Boulanger, Mahomet, IL (US); Zongbo Tong, Champaign, IL (US)

(72) Inventors: William Allen Boulanger, Mahomet, IL (US); Zongbo Tong, Champaign, IL (US)

( * ) Notice: Subject to any disclaimer, the term of this patent is extended or adjusted under 35 U.S.C. 154(b) by 0 days.

(21) Appl. No.: 18/539,688

(22) Filed: Dec. 14, 2023

(51) Int. Cl.
*A61K 31/42* (2006.01)
*C07D 261/12* (2006.01)

(52) U.S. Cl.
CPC ............ *A61K 31/42* (2013.01); *C07D 261/12* (2013.01)

(58) Field of Classification Search
CPC ............................... A61K 31/42; C07D 261/12
See application file for complete search history.

(56) References Cited

PUBLICATIONS

The Synthesis of Pantherine and Related Compounds By: Bowden, Kenneth; et al. Journal of the Chemical Society, [Section] C: Organic (1968), (2), 172-85.
A Convenient Synthesis of Muscimol by a 1,3-Dipolar Cycloaddition Reaction By: Chiarino, D.; et al. Tetrahedron Letters (1986), 27(27), 3181-2.
An Improved Synthesis of Muscimol By: Pevarello, P.; et al. Synthetic Communications (1992), 22(13), 1939-48.
Synthesis of N-Substituted Muscimol Derivatives Including N-Gycylmuscimol By: Frey, Michael; et al. Synthesis (1985), (12), 1100-4.
Synthesis of Pantherine (Agarin) By: Gagneux, A. R.; Häfliger, F.; Geigy, J. R.; Basle, S. A.; and Eugster, C. H.; Good, R.; *Tetrahedron Letters* No. 25, pp. 2077-2079. 1965.

*Primary Examiner* — Kamal A Saeed
(74) *Attorney, Agent, or Firm* — King & Partners, PLC

(57) ABSTRACT

Pharmaceutical intermediates and methods for efficiently preparing muscimol mono-BOC and derivatives thereof in the synthesis of muscimol and congeners and derivatives thereof.

2 Claims, 4 Drawing Sheets

Scheme 1

Scheme 2
The Improved Route to Muscimol

PHARMACEUTICAL INTERMEDIATES AND METHODS FOR PREPARING THE SAME IN THE SYNTHESIS OF MUSCIMOL AND CONGENERS AND DERIVATIVES THEREOF

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to novel pharmaceutical intermediates, including, but not limited to, muscimol mono-BOC (i.e., tert-butyl ((3-hydroxyisoxazol-5-yl)methyl)carbamate) and to methods for efficiently preparing the same in the synthesis of muscimol (i.e., agarin, pantherine, 5-(aminomethyl)isoxazol-3-ol) and congeners and derivatives thereof.

2. Background Art

Muscimol is a component of the mushroom *Amanita muscaria*, and is one of the active principle compounds it contains. It is considered a hallucinogen with possible therapeutic applications. Syntheses of muscimol have appeared from the late 1960's, but to date, none have been practical for either large scale manufacture or for manufacture under GMP conditions for pharmaceutical use. See, for example, Synthesis of pantherine and related compounds By: Bowden, Kenneth; et al. Journal of the Chemical Society [Section] C: Organic (1968), (2), 172-85., A convenient synthesis of muscimol by a 1,3-dipolar cycloaddition reaction By: Chiarino, D.; et al. Tetrahedron Letters (1986), 27(27), 3181-2., An improved synthesis of muscimol By: Pevarello, P.; et al. Synthetic Communications (1992), 22(13), 1939-48, and Synthesis of N-substituted muscimol derivatives including N-glycylmuscimol By: Frey, Michael; et al. Synthesis (1985), (12), 1100-4.

There are several reasons for this problem: muscimol as a free base is a very delicate compound that is freely soluble in water, making it very difficult to free it from the associated salts in its production. This can only be achieved by ion exchange chromatography. Some of the syntheses are very short, but depend upon the use of fulminate intermediates, which have a reputation for explosivity in the presence of certain metals. Other preparations require material not available in significant quantities.

One of the remarkable properties of muscimol is its pH sensitivity, which affects the process. Muscimol is extremely stable at low pH, but above pH 7, it rapidly decomposes, apparently via a polymerization. This means that if a hydrohalide form is produced initially, a base as weak as sodium bicarbonate to create the free base is sufficient to significantly reduce the yield on small scale, and to destroy the product completely on larger scale, where manipulation times are longer. Bench scale preparations use ion exchange chromatography, but this comes at a price of yield. The simple solution to this is to keep the product in the hydrohalide form, preferably hydrochloride, which is much more stable. This creates a new issue of how to purify the crude muscimol hydrochloride. This process addresses the issue both prior to the creation of muscimol proper, and at the final step.

The original 1966 preparation of muscimol by Bowden, et al, described a very plausible synthetic route to muscimol, but very few have been able to successfully reproduce it, much less scale it up. Nonetheless, it uses readily attainable materials, and is handled in a manner that is not inconsistent with larger scale. Their preparation, which targeted the free base, still required ion exchange chromatography to produce the clean product. With understanding of the behaviors in each step, and with certain key modifications, it is possible to use this original preparation as the nucleus of a reliable and scalable preparation of pure muscimol hydrochloride without having to resort to chromatography. The original route is illustrated in FIG. 1 (Scheme 1).

The starting material is readily available commercially, and the first step goes nearly quantitatively to form the stable dimethoxylketal. The ketal serves the double function of not only protecting the ketone, but also kinetically de-activating the neighboring chloride as a leaving group due to steric interference. Using published conditions, the hydroxylamine reaction proved to give poor yields and purity, residual hydroxyl amine carried through to later steps and proved problematic. The final two steps are also very problematic, and likely the reason for the reported irreproducibility. The authors provide scant detail for the ring closure reaction, and even in their hands, this reaction gave poor yields. In aqueous hydrochloric acid, the desired reaction pathway requires protonation of one of the ketal methoxy's, ring closure by displacement by the hydroxyl on the amide nitrogen, then protonation and elimination of the remaining methoxy to form the ring double bond. Competing with this mechanism is simple acid-catalyzed hydrolysis of the amide bond, leading to product loss.

In the final step, one of the vulnerabilities of muscimol comes into play. The original authors provided far too high a temperature under the circumstances. The chloride in this case is pseudo-benzylic, and thus very reactive, so the conversion to muscimol is correspondingly rapid. However, under the basic conditions, the nascent product is induced to alkylate again. This has the appearance in the mass spec of the product dimers and trimers. This significantly reduces yields and mandates purification.

There is an added issue, in that in the presence of an excess of ammonium hydroxide, the product mixture is not simply the pure hydrochloride of muscimol, but rather, a mixture of muscimol hydrochloride, muscimol free base, and ammonium chloride. In pharmaceutical preparations, the ammonium chloride is problematic as an impurity. A method to avoid the presence of ammonium hydrochloride in the product is required, but without the chromatography.

It is therefore an object of the present invention to provide novel methods for efficiently preparing pharmaceutical intermediates, including, but not limited to, muscimol mono-BOC (i.e., tert-butyl ((3-hydroxyisoxazol-5-yl)methyl)carbamate) and derivatives thereof in the synthesis of muscimol and congeners/derivatives thereof.

SUMMARY OF THE INVENTION

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

The present invention is directed to a compound/pharmaceutical intermediate, comprising, consisting essentially of, and/or consisting of the structure:

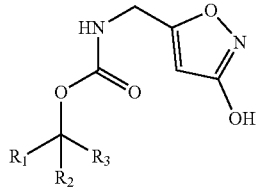

wherein $R_1$-$R_3$ are the same or different and selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkynyl group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof.

The present invention is also directed to a compound/pharmaceutical intermediate, comprising, consisting essentially of, and/or consisting of the structure:

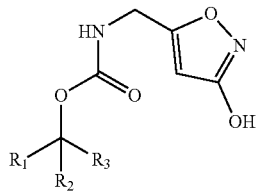

wherein $R_1$-$R_3$ are the same or different and selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkynyl group containing approximately 1 to approximately 25 carbon atom(s), with the proviso that at least two of $R_1$-$R_3$ comprise methyl groups.

The present invention is further directed to a compound/pharmaceutical intermediate, comprising, consisting essentially of, and/or consisting of the structure:

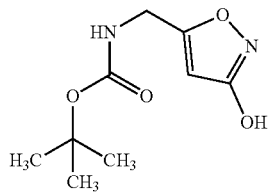

In a preferred embodiment of the present invention, the compound having the structure:

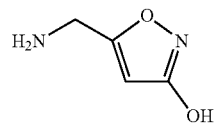

is prepared using the intermediate having the structure:

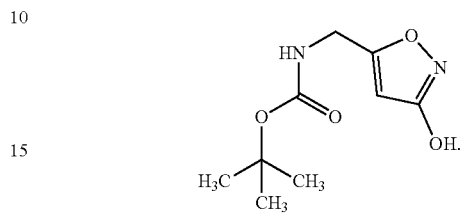

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted.

It will be further understood that the invention is not necessarily limited to the particular embodiments illustrated herein.

Figure 1:
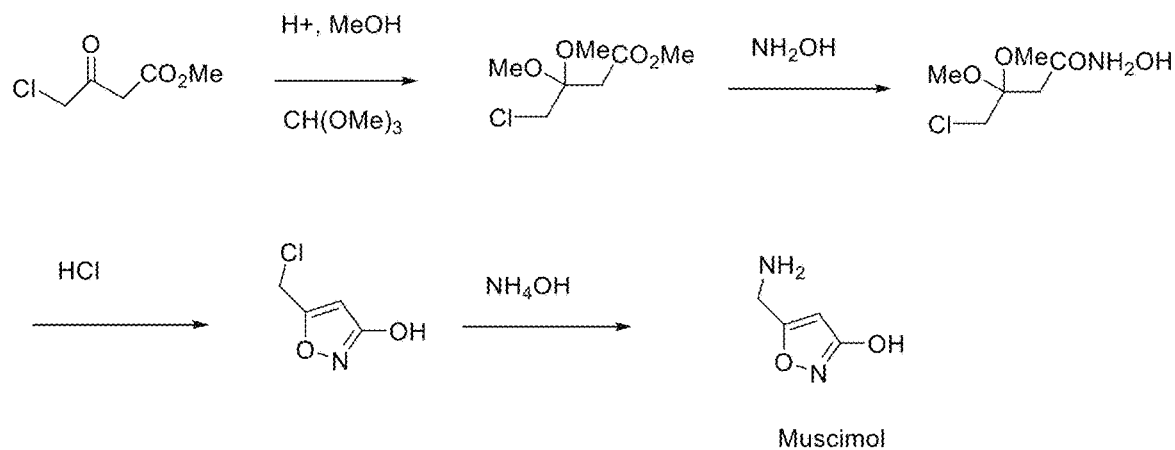
Figure 2:
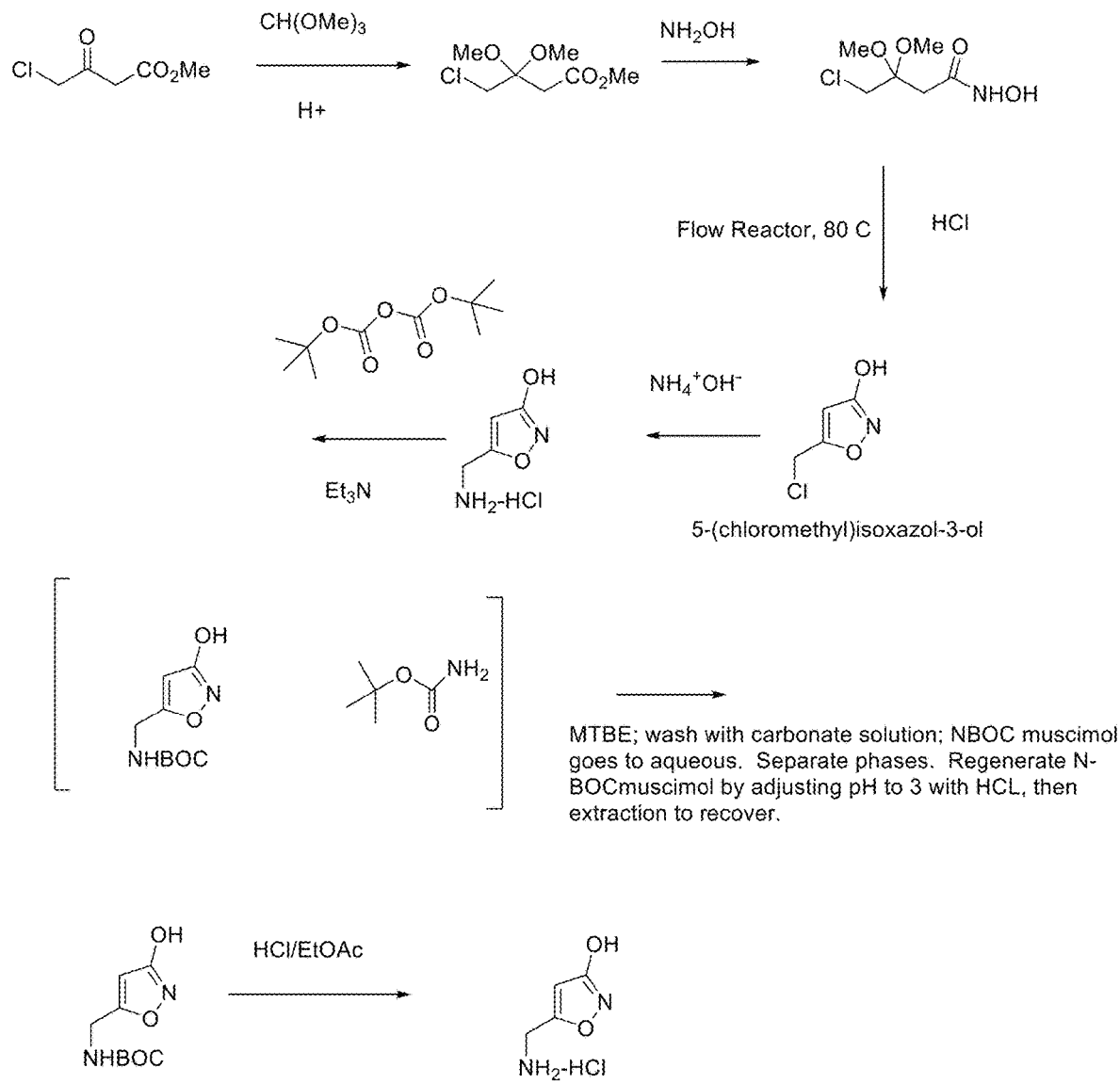
Figure 3:
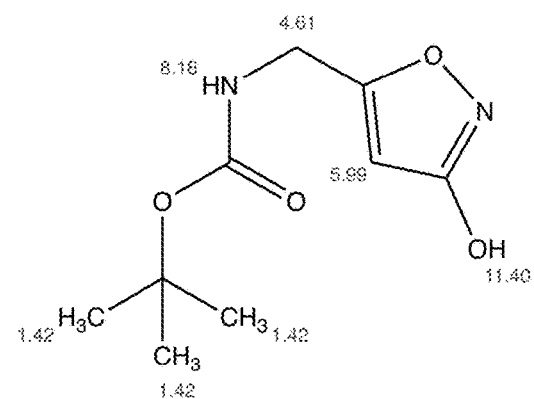
Figure 3:
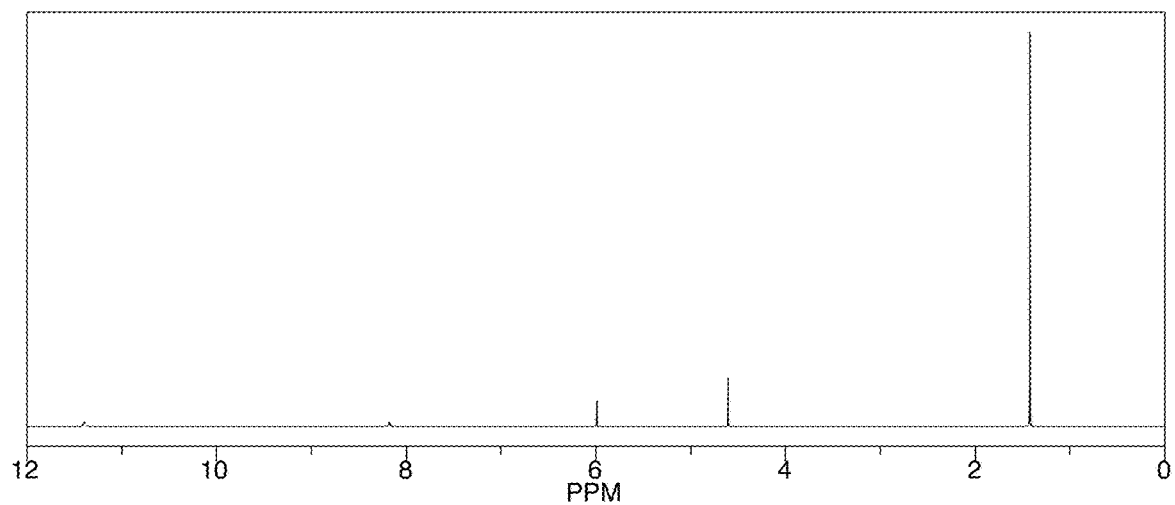
Figure 4:
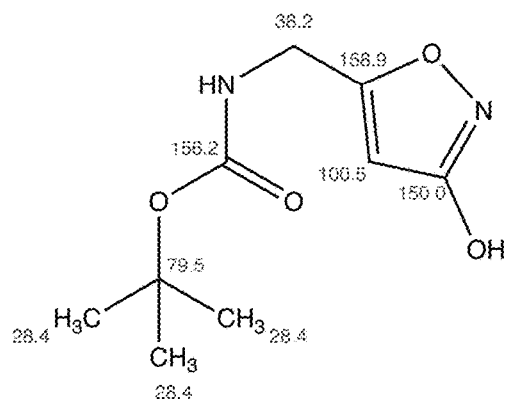
Figure 4:
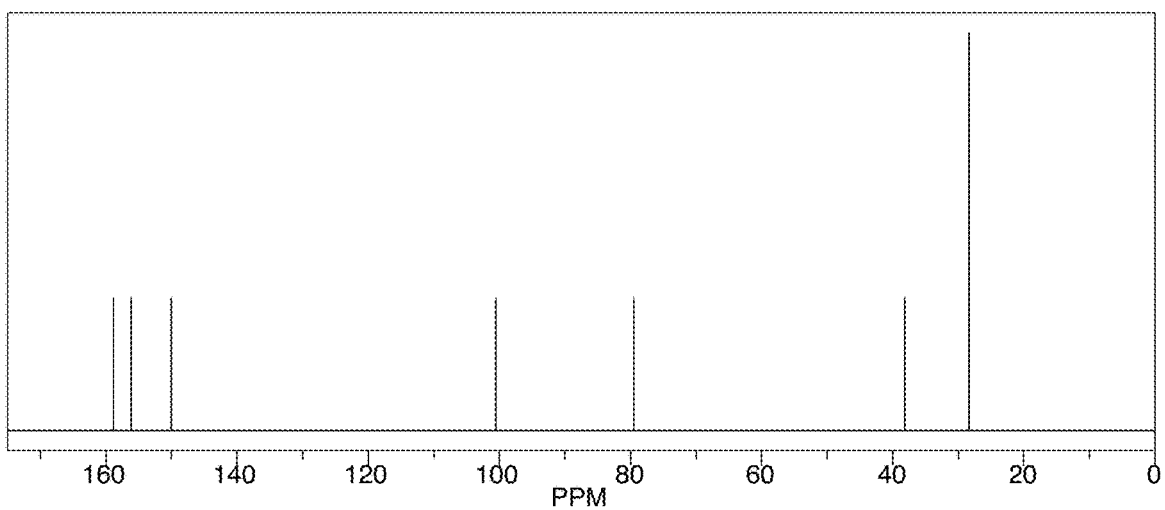

The invention will now be described with reference to the drawings wherein:

FIG. 1 of the drawings is a schematic flowchart for the synthesis of muscimol using the prior art route;

FIG. 2 of the drawings is a schematic flowchart for the synthesis of muscimol using a route of the present invention;

FIG. 3 of the drawings is a $^1$H-NMR spectrogram of muscimol mono-BOC prepared in accordance with the present invention; and FIG. 4 of the drawings is a $^{13}$C-NMR spectrogram of muscimol mono-BOC prepared in accordance with the present invention.

DETAILED DESCRIPTION OF THE INVENTION

While this invention is susceptible of embodiment in many different forms, there is shown in the structural formulas and described herein in detail several specific embodiments with the understanding that the present disclosure is to be considered as an exemplification of the principles of the invention and is not intended to limit the invention to the embodiments illustrated. It will be understood that the structural formulas disclosed herein are intended to comprise all stereochemical configurations regardless of graphical representations.

The present invention is directed to novel compounds/pharmaceutical intermediates, including, but not limited to, muscimol mono-BOC (i.e., tert-butyl ((3-hydroxyisoxazol-5-yl)methyl)carbamate) and to methods for efficiently preparing the same in the synthesis of muscimol (i.e. agarin, pantherine, 5-(aminomethyl)isoxazol-3-ol) and congeners and derivatives thereof. The route for preparing the compounds of the present invention is illustrated in FIG. 2 (Scheme 2).

In a preferred embodiment, the present invention is directed to a compound/pharmaceutical intermediate, comprising, consisting essentially of, and/or consisting of the structure:

5

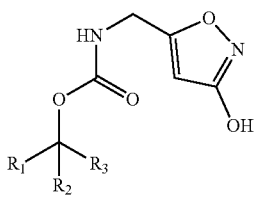

6

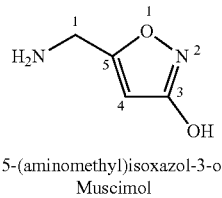

5-(aminomethyl)isoxazol-3-ol
Muscimol wherein R₁-R₃ are the same or different and selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkynyl group containing approximately 1 to approximately 25 carbon atom (s), wherein the carbon atom(s) may be a linking group to, or part of, a halogen, a N, O, and/or S containing moiety, and/or one or more functional groups comprising alcohols, esters, ammonium salts, phosphonium salts, and combinations thereof.

In another preferred embodiment, the present invention is directed to a compound/pharmaceutical intermediate, comprising, consisting essentially of, and/or consisting of the structure:

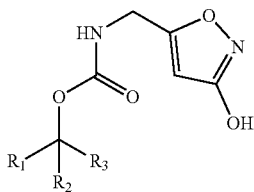

wherein R₁-R₃ are the same or different and selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkynyl group containing approximately 1 to approximately 25 carbon atom (s), with the proviso that at least two of R₁-R₃ comprise methyl groups.

In yet another preferred embodiment, the present invention is further directed to a compound/pharmaceutical intermediate, comprising, consisting essentially of, and/or consisting of the structure:

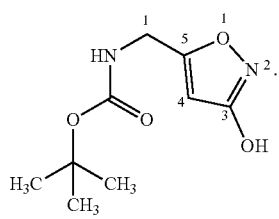

tert-butyl ((3-hydroxyisoxazol-5-yl)methyl)carbamate
Muscimol mono-BOC

In this embodiment the first tautomer of the compound generally comprises the ¹H-NMR spectrogram of FIG. 3 and/or the ¹³C-NMR spectrogram of FIG. 4.

In a preferred embodiment of the present invention, the compound having the structure:

is prepared using the above-identified intermediate.

Referring now again to Scheme 2 (FIG. 2) of the present invention and given the simplicity to prepare the dimethoxyketal, it can be considered a starting material here. The preparation of the hydroxylamide involves reducing the number of equivalents of hydroxylamine, gradually revealed as the free base, and allowing the reaction to run near room temperature. Under normal substitutions at a carbonyl by a nitrogen base, it is necessary to use large excesses of the nitrogen base, here as hydroxylamine. This is because nitrogen adds poorly to an sp2 center, and the weight of numbers must be used to push the reaction to completion. However, nitrogen is a very good displacing nucleophile at an sp3 center, where it can displace a leaving group. In this case, we use two equivalents of methoxide: first to free the amine hydrochloride, but the second one adds to the ester carbonyl. This makes a tetrahedral sp3 center, and from this, the methoxide can be displaced by the incoming nitrogen of hydroxylamine, resulting ultimately in the amide. Thus, only a small excess of hydroxylamine is required, and this mitigates the problems associated with hydroxylamine staying with the product and causing problems downstream in the scheme. The remaining small portion of hydroxylamine is captured as the acetone oxime by addition of excess acetone, and pH adjustment. The acetone oxime can be filtered out, along with the sodium chloride generated by the neutralization. After further concentration, and adding n-butanol, and re-concentration, it only requires recrystallization from ethyl acetate/hexanes to give high yields of crystalline product, free of residual hydroxylamine. This produces a hydroxylamide free of residual hydroxylamine which plagues the original synthesis by making intractable side products downstream.

To address the problem of low yields in the cyclization step, the exposure to concentrated HCl is preferably brief, and at an elevated temperature. What is more, if the concentrated HCl is removed by typical evaporation, even at low temperature, the required time at elevated temperature favors hydrolysis. However, the product can be extracted from subsequently diluted HCl by use of a solvent, such as ethyl acetate or isopropyl acetate, and any carried-over HCl can be washed away with brine from the extracts. To achieve these two conditions, a flow reactor is used. The reaction naturally off-gasses both HCl and methyl chloride as it proceeds, so some arrangement must be created where gas can be removed, but not be allowed to push the liquid prematurely through the reactor. This is achieved by passing the reaction fluid through a series of vented cells in a heated bath. Two basically different designs of such cells were used. Each cell was configured such that the liquid enters on the bottom of the cell, slowly rises up, then overflows into the next cell. Optimally, each cell stage has its own metering pump in, so that the system does not rely on gravity alone. In practice, only four cells were used on a very slow flow set-up (total residence time 35 minutes), but more cells or larger cells can be used for a faster through-put. A solution of the hydroxylamide is prepared at ambient temperature, and fed into a series of four cells suspended in a bath at 80° C. for a period between 25 and 50 minutes residence time, then immediately taken through a cold bath at ice temperature and diluted, at which point a solvent such as ethyl acetate or isopropyl acetate is introduced and put through a static mixer, then sent cold to a receiver. There the first extraction is removed, and the aqueous layer extracted twice more with the same solvent. The combined extracts are then washed with brine twice to remove residual HCl, and the crude chloroisooxazole is recovered by removal of the solvent. This method has the advantage of a small footprint, is a continuous operation, and is capable of considerable scaling up.

Alternately, this can be run batch-wise, with the concentrated HCl solution being introduced into a larger volume of water, where it is diluted. When the HCl concentration reaches 2 M, the mixture is extracted as described above.

On the very small scale, such as 10 g, a flow reactor is not necessary, and the reaction can be run in a simple heat-regulated flask protected from air, but with a gas-release, such as a bubbler.

The remainder of the synthesis has been modified to minimize and eliminate the multiple alkylation in the amination, and to eliminate the ammonium chloride in the final product. The chloroisooxazole is not a very stable compound, and must be reacted immediately in the next step.

One should note that in concentrated HCl, it is capable of being protonated itself, and this form is particularly unstable. The unprotonated form is relatively more stable. The compound is nonetheless quite acidic, due to its tendency to adopt aromaticity through its tautomer. Thus, it can only be extracted from the aqueous in conditions approximating 2M HCl.

The amination can be run with between 20 and 30 equivalents of ammonium hydroxide in the absence of organic co-solvents at 20-25° C. Organic co-solvents strongly promote dimer or trimer formation. The residual ammonium hydroxide is removed with good vacuum below 45° C., to give the crude muscimol. These conditions promote decomposition of the muscimol as the scale increases, even though they work quite well on the 100 g scale. By switching to saturated ammonia in methanol, and reacting at 45° C.-50° C., with slight pressure containment, these deleterious conditions are avoided, and the excess ammonia and the solvent methanol are easily removed.

In either case, however, this amination gives a mixture of muscimol hydrochloride, free base, and ammonium chloride. This crude mixture must be treated with BOC anhydride (Di-tert-butyl decarbonate) and triethylamine. This forms a mixture of N-BOC muscimol, and tert-butylcarbamate. If the mixture is dissolved in MTBE, the contaminating tert-butylcarbamate will be left in the organic phase if it is extracted with dilute sodium carbonate, the N-BOC muscimol is extracted into the aqueous phase due to its acidity. After separation of layers, the pH may be adjusted to about pH 3 with concentrated HCl, releasing the N-BOC muscimol. This may be recovered by extraction, leaving clean mono BOC muscimol as a solid after solvent removal. As the N-BOC muscimol is unstable to prolonged exposure to low pH, this must be done expeditiously. This step removes the residual latent ammonia that appeared in the product of previous preparations. The crude N-BOC muscimol may be further purified by recrystallization from a solvent system like MTBE/hexanes or ethyl acetate/hexanes. MP 134.5-137.5° C.

This now clean monoBOC muscimol may be dissolved in either ethyl acetate or isopropyl acetate or similar solvent, and decomposed by the introduction of HCl gas in near-stoichiomeric amounts. The product muscimol hydrochloride falls out as crystals, harvestable by filtration. By direct formation of the very stable hydrochloride, the unstable free base form is avoided.

EXAMPLES

Preparation of the methyl 4-chloro-3,3-dimethoxy-butanoate

A 72-L round-bottom flask was set up with a heating mantle, mechanical stirrer, addition funnel, and reflux condenser. To the flask was charged methyl 4-chloroacetoacetate (5 Kg, 33.2 mol), trimethylorthoformate (7.27 L, 66.42 mol), and methanol (40 L, 8:1). Trifluoromethane sulfonic acid (500 g, 340 mL, 3.32 mol) was slowly dripped in with stirring over 30 min. The mixture then was refluxed overnight (12 hrs). Completion was determined by TLC (20% ethyl acetate in hexanes; silica gel, UV) vs the starting ketone. The reaction mixture was cooled down to room temperature, then concentrated by half using a rotary evaporator. The residue was neutralized by slow addition of the concentrate to a suspension of sodium carbonate (194 g, 1.826 mol. 0.55 eq) in 8 L water. The neutralized reaction mixture is extracted 3 times with a 1:1 mixture of hexanes/ethyl acetate (5 L each). The combined extracts were dried over sodium sulfate, filtered, then concentrated to give the crude Methyl 4-chloro-3,3-dimethoxy butanoate, 5.8 Kg, 89%.

Preparation of 4-chloro-N-hydroxy-3,3-dimethoxybutanamide

A small 3 neck flask was set up with a magnetic stirrer, dropping funnel, thermoprobe, and empty ice bath. To the flask was added methyl 4-chloro-3,3-dimethylbutanoate (2 g, 10 mmol) and methanol (3.3 g, 4.16 mL). The mixture was cooled to 15° C., and hydroxylamine hydrochloride (1.02 g, 14.7 mmol) was added all at once. Sodium methoxide, 30% in methanol (5.327 g, 29.6 mmol) was charged to the addition funnel and added over 2-3 hrs, while keeping the temperature between 15 and 25° C. The reaction was then stirred at 20° C. for 12 hrs. Then the reaction was cooled to 0-5° C. HCl gas was introduced to bring the pH to 5. Acetone (0.853 g, 14.7 mmol) was added all at once, and the mixture stirred at pH 5 for two hours at 10-15° C. The pH was then adjusted to 6-7 with sodium methoxide solution, and the mixture cooled down to 0-5° C. This precipitated a mixture of sodium chloride and acetone oxime, which was removed by filtration, the solids were washed with methanol. Using a water bath on the rotary evaporator at 40° C., the filtrate was reduced in volume by 73%. The mixture was diluted with a little n-butanol, then re-concentrated, removing about 80% of the volume. 6 L of 88:1 ethyl acetate:methanol were added, then the mixture was reconcentrated. Then 7 L ethyl acetate were added, and the mixture brought to 55° C. The mixture was cooled to 0° C., then filtered. The mother liquors were concentrated ands cooled as before, giving a second crop. 4.2 K 87.5% yield.

Preparation of 4-chloro-N-hydroxy-3,3-dimethoxybutanamide

A 22-L round-bottom flask was set up with a mechanical stirrer, addition funnel, and thermoprobe. A solution of methyl 4-chloro-3,3-dimethoxy-butanoate (1.0 Kg, 5.1 mol) in methanol (2 L) was charged to the flask. Hydroxylamine hydrochloride (509 g, 7.32 mol, 1.44 eq) was added to the flask all at once, with stirring. Sodium methoxide, 30% in methanol (2.65 kg solution, 14.75 mol, 2 eq vs ketal) was charged to the addition funnel, and added slowly over 2 hrs, 45 minutes. Temperature at end of addition: 17.1° C. The mixture was then allowed to stir at ambient temperature (21° C.) overnight (12 hrs). Completion was determined by TLC vs the starting ketal (20% ethyl acetate/hexanes, silica gel, UV). The pH of the solution was adjusted to 5-6 with HCl gas (exothermic). Acetone (540 mL, 425 g, 1.44 eq) was added all at once, and the mixture stirred at 20° C. for 2 hours. The resulting solids were removed by filtration, and washed with a little methanol to recover clinging product. The solution was concentrated approximately 75% (40° C.) under reduced pressure. n-Butanol (400 mL) was added, and the mixture reconcentrated as much as possible. Then a mixture of 88% ethyl acetate/12% methanol was added; this was then stripped down nearly completely. Finally, ethyl acetate (8 L) was added, and the mixture heated at 45° C. to dissolve the crude product as much as possible; this mixture was then brought to 0° C., and kept there until the product had fully crystallized. The mixture was filtered to harvest a first crop of product. The mother liquors were concentrated, cooled as before, and a second crop of product obtained. These were combined, and dried, giving 870 g, 87% yield of 4-chloro-N-hydroxy-3,3-dimethoxybutanamide.

Preparation of 5-(chloromethyl)isooxazol-3-ol

The cyclization is easily achieved on a benchtop scale with classical equipment, but problematic on a production scale using the same technology due to the longer heating times required. This is one of the original reasons for failure of this synthesis to be successfully scaled up. Use of a special multi-celled flow reactor solves this problem.

Bench Scale Cyclization:
A magnetically stirred 100 mL round bottomed flask with a reflux condenser, septum, and hypodermic needle pressure relief, was set up with a temperature-controlled oil bath. The flask was charged with 4-chloro-N-hydroxy-3,3-dimethoxybutanamide (10 g, 50.7 mmol) prepared by the improved method, and 50 mL 12 M HCl. After 10 minutes at 80° C., HPLC analysis of a sample showed 93% product. The reaction was stopped and cooled, diluted with water, then extracted three times with ethyl acetate. The extracts were washed twice with brine, dried over sodium sulfate, filtered, then the solvent removed in vacuo, giving off-white crystals of 5-(chloromethyl)isoxazol-3-ol, g, 91% by HPLC.

Flow Reactor:
For this run, glass reactor cells of 30 mm diameter, 200 mm deep from the side-arms, having 12 mm OD side tubing were used. Four were used in series, and all immersed in a regulated hot water bath at 80° C. The cells were connected with polypropylene tubing, and the vents on top were provided with 0.5 M tubing straight up. The feed pump was an FMI plastic and ceramic metering pump, adjusted to give a residence time of 55 minutes in the system. The outflow of the reactor was collected in a nitrogen-protected flask containing 300 mL isopropyl acetate.

A mixture of 4-chloro-N-hydroxy-3,3-dimethoxybutanamide (50 g, 0.308 mol) and 10 M HCl (370 mL, 10 eq's) was prepared, and metered into the series of flow reactors over approximately 1 hr. To chase the system, another 400 mL of brine was then metered through, while still at 80° C. When the brine flush had completed, the mixture in the receiver was thoroughly mixed, and the isopropyl acetate removed. The aqueous layer was extracted twice more with isopropyl acetate (300 mL), giving a solution of crude 5-(chloromethyl)isoxazol-3-ol. This was immediately combined with 500 mL concentrated ammonium hydroxide, and stirred for 3 hrs at room temperature (20° C.). HPLC showed the reaction nearly complete at 2 hrs, but no change with the extra hour. The organic phase was then removed, and the aqueous phase concentrated at 40° C. and 1 mm, using very good venting to relieve the ammonia gas released. Recovered crude muscimol, 20.0 g, of 69% purity by HPLC.

Preparation of Crude Muscimol

An isopropyl acetate extract of freshly prepared 5-(chloromethyl)isoxazol-3-ol, estimated to contain 154 g (1.16 mol) of material, was mixed at 20° C. with concentrated ammonium hydroxide (2.5 L). HPLC indicated that after 3 hrs, the reaction was complete. The organic layer was removed, and the aqueous layer was concentrated at 40° C./1 mm, with provision to vent the off-gassed ammonia. This provided 143 g crude muscimol.

Preparation of Crude Muscimol

To a 1-gallon hastalloy autoclave cooled with dry ice, 100 g of the chloride was added. 1.2 L of methanol saturated with ammonia at 0° C. was poured into the autoclave. Then the autoclave was sealed, and the temperature increased to 40° C., with the natural pressure build-up reaching 50 psi. The mixture was allowed to stay at 40° C. for 12 hrs, then cooled. An HPLC analysis showed total conversion to muscimol. The solution was then evaporated to almost dry, giving 50 g crude muscimol hydrochloride.

Preparation of N-BOC Muscimol

A total of 135 g of crude muscimol (1.18 mol) was dissolved in 3.5 L of methanol. To this was added triethylamine (240 g, 2.37 mol) and BOC anhydride (248 g, 1.3 mol) in small portions. An ice bath was used to cool the reaction's exotherm to 40° C. The mixture was stirred at room temperature until determined to be complete by HPLC (about 1 hr).

The reaction mixture was stripped of solvent, and the residue dissolved in 1.5 L distilled water. The pH was adjusted to pH 3.5 with 0.5M HCl. This was extracted 4 times with 1:1 ethyl acetate/MTBE. All of the organic phases were combined, washed twice with 1 L water. Then the organic layer was extracted 2×750 mL saturated sodium carbonate. The product is now in the aqueous. The aqueous layer was washed 2×500 mL MTBE to remove impurities. Then the pH of the aqueous was adjusted to 2-3 with 2 N HCl, and extracted 3×1 L 1:1 Ethyl acetate:MTBE. The organic extracts were dried over sodium sulfate, filtered, and concentrated. This gave a light yellow solid. This was dissolved in 250 mL ethyl acetate at 40° C., filtered, and kept at −20° C. overnight. This gave a beautiful crop of crystals, which upon filtering and drying, gave 70 g, 58% yield.

Preparation of N-BOC Muscimol, then Muscimol

In a nitrogen-protected magnetically-stirred round-bottomed flask, crude muscimol (100 g, 0.877 mol) was dissolved in methanol (1 L). To this solution was added triethyl amine (177 g, 1.75 mol), then BOC-anhydride (82.6 g, 0.379 mol). After 30 minutes, the reaction was checked by HPLC, and shown to be complete. Excess MTBE was added, and 0.1 M HCl to pH 3. The product was in the MTBE. Removed the aqueous layer. The organic phase was extracted twice with 0.3M sodium carbonate, drawing the product into the aqueous phase. The aqueous phase was washed with MTBE, then acidified with 2 NHCl and extracted twice with ethyl acetate. The product is now in the ethyl acetate.

Into the ethyl acetate solution was introduced a slow stream of HCl gas. This was an exothermic reaction, so it had to be cooled in ice. With time and cooling, muscimol hydrochloride precipitated. This was recovered by filtering and drying. Recovered 23.4 g of muscimol hydrochloride, suitable for further purification by recrystallization.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A pharmaceutical intermediate having the structure:

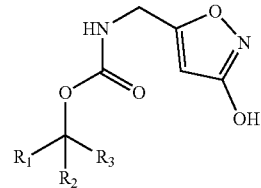

wherein $R_1$-$R_3$ are the same or different and selected from the group consisting of H; OH; and an alkyl, cycloalkyl, polycycloalkyl, heterocycloalkyl, aryl, alkaryl, aralkyl, alkoxy, alkanoyl, aroyl, alkenyl, or alkynyl group containing 1 to 25 carbon atom(s), with the proviso that at least two of $R_1$-$R_3$ comprise methyl groups.

2. A pharmaceutical intermediate having the structure:

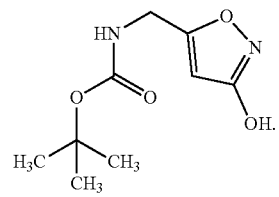

* * * * *